United States Patent [19]

Castaldi et al.

[11] Patent Number: 4,535,166

[45] Date of Patent: Aug. 13, 1985

[54] PROCESS FOR PREPARING ALPHA-ARYLALKANOIC ACIDS

[75] Inventors: Graziano Castaldi, Briona; Claudio Giordano, Vicenza, both of Italy

[73] Assignee: Zambon S.p.A., Vicenza, Italy

[21] Appl. No.: 520,131

[22] Filed: Aug. 3, 1983

[30] Foreign Application Priority Data

Aug. 6, 1982 [IT]  Italy .............................. 22760 A/82
Mar. 7, 1983 [IT]  Italy .............................. 19930 A/83

[51] Int. Cl.$^3$ ............................................ C07C 67/333
[52] U.S. Cl. .................................. 548/204; 548/217; 548/444; 548/562; 549/79; 560/55; 560/56; 560/105; 562/465; 562/466; 562/496
[58] Field of Search ............................ 560/56, 55, 105; 562/465, 466, 496; 549/79; 548/204, 217, 444, 562

[56] References Cited

U.S. PATENT DOCUMENTS 4,414,405  11/1983  Giordano .............................. 560/56

FOREIGN PATENT DOCUMENTS 89711  9/1983  European Pat. Off. .............. 560/56

OTHER PUBLICATIONS

March, Advanced Organic Chemistry, pp. 991–995, (1977).

*Primary Examiner*—Robert Gerstl
*Attorney, Agent, or Firm*—Cushman, Darby & Cushman

[57] ABSTRACT

Rearrangement of alpha-halo-alkylarylketals in neutral or weakly alkaline conditions and in the presence of a polar-protic medium and subsequent hydrolysis of the thus obtained esters, in the same reaction medium, to afford the corresponding alpha-arylalkanoic acids or their salts which are particularly useful as anti-inflammatory, analgesic and antipyretic agents.

6 Claims, No Drawings

PROCESS FOR PREPARING ALPHA-ARYLALKANOIC ACIDS

This invention relates to a process for preparing an alpha-arylalkanoic acid or a salt thereof which comprises the rearrangement of an alpha-halo-alkylarylketal in neutral or weakly alkaline conditions and in the presence of a polar-protic medium and the subsequent hydrolysis of the thus obtained ester in the same reaction medium to afford the corresponding alpha-arylalkanoic acid.

The European patent application No. 34871 describes a process for preparing esters of alpha-arylalkanoic acids via rearrangement of alpha-halo-alkylarylketals in the presence of a Lewis acid. The disadvantages of this process are that the reaction must be carried out in an anhydrous medium and that the more effective Lewis acids are the salts of toxic heavy metals; consequently there is a need for a careful purification when the final produce is intended for pharmaceutical use. This purification step may be carried out sucessfully by isolating the ester but this impairs the compaction of both the rearrangement and the hydrolysis steps.

Furthermore the Lewis acids incline to ineract with the oxygen atoms of the ketal group and, consequently, to form by-products whose amount ranges in accordance with the nature of the alpha-halo-alkylarylketal and of the Lewis acid which are used.

The European application No. 48.136 describes a process for preparing alpha-arylalkanoic acids wherein an alpha-sulfonyloxyketal undergoes hydrolysis. This process lays on the prejudice that the halogen atom is not sufficiently labile to promote the rearrangement in the absence of a catalyst having affinity for halogen whereas it was well known that the sulfonyloxy-groups like the tosyloxy and mesyloxy are sufficiently labile to disassociate from the substrate upon contact with a protic-polar medium.

Despite the apparent easy of the last step this process is complex and cumbersome owing to the face that at first an alpha-halo-ketone is reacted with an alkali metal alkoxide to afford an alpha-hydroxyketal which is then treated with an O-sulfonylating agent to form the corresponding alpha-sulfonyloxyketal and finally the alpha-sulfonyloxyketal is submitted to hydrolysis. The number of steps involved and the difficulties inherent in carrying out on a large scale some of the steps leave room for a more simple and economical process.

Now it has been surprisingly found that the alpha-haloalkyl aryl ketals undergo rearrangement in neutral or weakly alkaline conditions and in the presence of a protic-polar medium thus avoiding the detour depicted by the European patent application No. 48.136 as well as disadvantages inherent in the process described by the European patent application No. 34.871.

More particularly the process according to this invention comprises the rearrangement of an alpha-haloalkylarylketal in neutral or weakly alkaline conditions and in the presence of a polar protic medium and the subsequent hydrolysis of the thus obtained ester in the same reaction medium to afford the corresponding alpha-arylalkanoic acid or a salt thereof.

The neutral or weakly alkaline condition is obtained by adding buffers or weak bases either organic or inorganic or mixture thereof. Examples of typical compounds are the aliphatic and the aromatic tertiary amines and the alkali and alkaline earth metals salts of organic and inorganic acids such as sodium bicarbonate, calcium carbonate, potassium acetate, triethylamine, methylpiperidine, methyl pyrrolidine and dimethylaniline.

The protic-polar media according to this invention are water, alcohols and mixtures thereof. Examples of alcohols include $C_1$-$C_{12}$ primary, secondary and terziary alcohols and $C_2$-$C_{12}$ polyhydric alcohols such as methanol, ethanol, butanol, isobutanol, sec butanol, 2-decanol, allyl alcohol, ethylene glycol, 1,2-propanediol, 1,3-propanediol, 1,10-decanediol, cis-2-buten-1,4-diol and the like.

Preferably the choice of the protic medium will depend from its lipophilic and hydrophilic properties as well as from the nature of the alpha-halo-alkylaryl ketal.

As a rule a decrease in the concentration of the hydroxy-groups such as in the alcohol and diols having a long aliphatic chain increases the lipophilic property of the protic medium and in its turn promotes the solubilization of the low-polar ketals but reduces their reaction rate which, on the contrary is favored by strongly hydrophilic protic media. Of course, the reaction rate is increased also by an increase in the reaction temperature.

Usually the reaction time is comprised between few minutes and about twelve hours when a ketal endowed with a normal reactivity is treated at a temperature from 80° to 200° C.

When the rearrangement is complete the pH of the reaction mixture is made acid or basic for hydrolyzing the ester. Preferably the pH is increased by addition of a base. Example of suitable bases include alkali and alkaline earth metal hydroxides and salts. Usually this step is complete in a time period comprised from few minutes and some hours at a temperature from 20° to 100° C. It is so obtained a salt of an alpha-arylalkanoic acid which is then treated, when desired, with an acid to afford the free alpha-arylalkanoic acid.

Examples of arylalkanoic acids which may be prepared with the process of this invention include aclofenac, benoxaprofen, caroprofen, diclofenac, fenclofenac, fenoprofen, fentiazac, flurbiprofen, indoprofen, ibuprofen, isoprofen, ketoprofen, naproxen, piroprofen, suprofen, tolmetin, xenbucin and the like.

The preferred ketals used as starting products according to this invention have the following formula

wherein $A_r$ is an aromatic ring selected from the group comprising (a) a phenyl ring substituted by one or two substituents selected from the group comprising halogen, 1-6 C alkyl, 1-4 C alkoxy, 2-4 C alkenyloxy, phenyl, phenoxy, dichlorophenoxy, dichloroanilino, benzoyl, indolinyl, dihydropyrrolyl, thenoyl (b) a naphthyl ring substituted by one or two substituents selected from the group comprising halogen and 1-4 C alkoxy (c) a pyrrolyl ring substituted by one or two radicals selected from the group comprising 1-4 C alkyl and alkyl$_{1-4}$ c-phenyl, (d) chloro-carbazolyl, (e) benzoxazolyl substituted by one chlorophenyl radical, (f) thiazolyl substituted by one or two radical selected from the group comprising phenyl and chlorophenyl, and (g) thienyl, R' and R", independently from each other, are a satured or unsatured, straight or branched alkyl radical having from 1 to 12 C atoms or, when taken together, are a satured or unsatured straight or branched alkylene radical having from 2 to 12 C atoms which completes an alicyclic ring having from 5 to 7 members, X is halogen;

R''' is hydrogen, alkyl having from 1 to 6 C atoms or cycloalkyl having from 1 to 7 C atoms.

The alpha-halo-alkylarylketals may be prepared according to known methods.

Examples of methods suitable for preparing alpha-halo-alkylarylketals contemplate the use of an acid catalyst such as p-toluenesulfonic acid (J. Org. Chem. 21, 1366 (1956); ibidem, 22, 662, (1957); Synthesis 23, (1974), active montmorillonite (Bull. Soc. Chim. France, 2558, (1975), $BF_3$ etherate (Bull. Soc. Chim. France 1763 (1975)) and citric acid (U.S. Pat. No. 3,936,398). An improvement to the last method contemplates the use of citric acid in the presence of hydroquinone which acts as polymerization inhibitor (Bull. Soc. Chim. France, 1973 (1975)).

The water generated in the course of the reaction is removed by azeotropic distillation with suitable solvents such as benzene, toluene, cyclohexane and the like or by means of a dehydrating agent such as anhydrous $CuSO_4$, a trialkylorthoformate, molecular sieves and the like (Synthesis, 501 (1981).

Other known methods for preparing the ketals are the trans-ketalization, the reaction of a ketone with an alcohol in the presence of a ketal such as 2,2-dimethoxypropane and an acid catalyst (J. Org. Chem. 25, 521 (1960)) and the reaction of an alcohol with a suitable enol-ether in the presence of an acid catalyst (Bull. Soc. Chim. France, 264 (1979)).

Examples of known alpha-halo-alkylarylketals include:

2-bromo-1,1-dimethoxy-1-(6'-methoxy-2'-naphthyl)-propane, 2-bromo-1,1-dimethoxy-1-(4'-isobutylphenyl)-propane, 2-(1'-bromoethyl)-2-(6'-methoxy-2'-naphthyl)-1,3-dioxane, and 2-(1'-bromoethyl)-2-(6'-methoxy-2'-naphthyl)-1,3-dioxolane.

Examples of not-yet described alpha-halo-alkylarylketals which are prepared according to known techniques are:

2-bromo-1,1-dimethoxy-1-(4'-methoxyphenyl)-propane
$^1$H-NMR (60 MHz) (CDCL$_3$—TMS) delta (ppm): 1,45 (d, 3H); 3,15 (s, 3H); 3.8 (s, 3H); 4.5 (q, 1H); 6.85–7.6 (m, 4H).

2-bromo-1,1-dimethoxy-1-(4'-isobutylphenyl)-propane
$^1$H-NMR (60 MHz) (CDCl$_3$—TMS) delta (ppm); 0.9 (d, 6H); 1.5 (d, 3H); 1.7–2.2 (m, 1H); 2.6 (d, 2H); 3.2 (s, 3H); 3.4 (s, 3H); 4.5 (q, 1H); 7.1–7.6 (m, 4H).

2-(1'-bromoethyl)-5,5-dimethyl-2-(6-methoxy2'-naphthyl)1,3-dioxane, m.p. 89°–90° C.

2-(1'-bromoethyl)-2-(4'-methoxyphenyl)1,3-dioxane $^1$H-NMR (60 MHz) (CDCl$_3$—TMS) delta (ppm): 1.65 (d, 3H), 3.6–4 (m, 6H); 3.85 (s, 3H); 4.1 (q, 1H); 7–7.7 (m, 4H).

2-(1'-bromoethyl)-2-(6'-methoxy-2'-naphthyl)-1,3-dioxane $^1$H-NMR (60 MHz) (CDCl$_3$—TMS) delta (ppm): 1.20 (m, 2H); 1.68 (d, 3H); 3.90 (m, 4H); 3.96 (s, 3H); 4.30 (q, 1H); 7.12–7.98 (m 6H).

2-bromoethyl)-5-(2'-butyl)-5-methyl-2-(4'-methoxyphenyl)-1,3-dioxane, 2-(1'-bromoethyl)-5,5-dimethyl-2-(4'-isobutylphenyl)-2,3-dioxane, b.p. 135°–138° C. (0,6 mm Hg)

2-(1'-bromoethyl)-5,5-dimethyl-2-(5'-bromo-6'-methoxy-2'-naphthyl)-1,3-dioxane, m.p. 143°–145° C.

2-(1'-bromoethyl)-5,5-dimethyl-2-(2'-thienyl)-1,3-dioxane, b.p. 78°–80° C. (0,5 mm Hg)

2-(1'-bromoethyl)-2-(4'-methoxyphenyl)-1,3-dioxolane
$^1$H-NMR (60 MHz) (CDCl$_3$—TMS) (ppm); 1.6 (d, 3H), 3.8 (s,3H); 3.8–4.2 (m, 4H); 4.4 (q, 1H); 6.85–7.6 (m, 4H)

Particularly useful new alpha-halo-alkylarylketals of formula I are those where R' and R" together are a straight or branched unsaturated alkylidene radical which forms a ring having 7 members. They are described by the Italian Patent Application No. 19930 A/83 filed on Mar. 7, 1983 and are an object of the U.S. patent application No. 520,130 filed on Aug. 3, 1983.

The following example are given to illustrate this invention without limiting it in any way.

EXAMPLE 1

2-(6'-methoxy-2'-naphthyl)-propionic acid (a) A mixture of 2-bromo-1,1-dimethoxy-2-(6'-methoxy-2'-naphthyl)-propane (3.39 g; 0.01 mol), potassium acetate (1.2 g; 0.012 mol) and 1,10-decane diol (5 g) is heated to 170° C. for six hours.

After having reduced the temperature to 70° C. and added 30% potassium hydroxide, the reaction mixture is heated to 100° C. for five hours. The mixture is then cooled to room temperature, poured into water (100 ml) and extracted with methylene chloride (3×100 ml).

The aqueous layer is acidified with concentrated hydrochloric acid to afford a precipitate consisting of 2-(6'-methoxy-2'-naphthyl)-propionic acid (1.38 g; 0.006 mol). Yield, 60%; m.p. 155°–156° C.

(b) By substituting ethylene glycol (40 ml) for 1,10-decanediol in the procedure of Example 1a and otherwise heating the reaction mixture to 125° C. for 8 hours, there is obtained the title product (1.9 g; 0.0082 mol). Yield, 82%; m.p. 155°–157° C.

(c) By substituting allyl alcohol (50 ml) for 1,10-decanediol in the procedure of example 1a and otherwise refluxing the reaction mixture for 48 hours, there is obtained the title product (1.2 g; 0,0052 mol). Yield, 52%; m.p. 155°–156° C.

(d) A mixture of 2-(1'-bromoethyl)-2-(6'-methoxy-2'-naphthyl)-1,3-dioxolane (3.37 g; 0.01 mol), potassium acetate (1.2 g; 0.012 mol) and ethylene glycol (50 ml) is heated to 125° C. for 16 hours.

By following the procedure of Example 1a, there is obtained the title product (1.61 g; 0.007 mol). Yield, 70%; m.p. 155°–156° C.

(e) A mixture of 2-(1'-bromoethyl)-2-(6'-methoxy-2'-naphthyl)-1,3-dioxolane (2.68 g; 0.008 mol), disodium phosphate (1.36 g; 0.0095 mol), monopotassium phosphate (1.44 g; 0.01 mol) and ethylene glycol (40 ml) is heated to 125° C. for 16 hours. By following the procedure of Example 1a, there is obtained the title product (1.25; 0.005 mol). Yield, 62,5%; m.p. 155°–156° C.

(f) A mixture of 2-(1'-bromoethyl)-2-(6'-methoxy-2'-naphthyl)-1,3-dioxolane (13.48 g; 0.042 mol), potassium bicarbonate (6 g; 0.06 mol) and ethylene glycol (200 ml) is heated to 125° C. for 18 hours.

By following the procedure of Example 1a, there is obtained the title product (6.91 g; 0.03 mol). Yield, 71,5%; m.p. 155°–156° C.

(g) A mixture of 2-(1'-bromoethyl)-2-(6'methoxy-2'-naphthyl)-1,3-dioxane (3.51 g; 0.01 mol), potassium acetate (1.2 g; 0.012 mol) and 1,3-propanediol (50 ml) is heated to 125° C. for 8 hours. By following the procedure of Example 1a, there is obtained the title product (2.25 g; 0.0098 mol). Yield, 98%; m.p. 155°–156° C.

(h) A mixture of 2-(1'-bromoethyl)-5,5-dimethyl-2-(6'-methoxy-2'-naphthyl)-1,3-dioxane (3.79 g; 0,01 mol), potassium acetate (1.2 g; 0,012 mol) and ethylene glycol (40 ml) is heated to 125° C. for 4 hours.

By following the procedure of Example 1a, there is obtained the title product (2.1 g; 0.0091 mol). Yield, 91%; m.p. 154°–155° C.

(i) A mixture of 2-(6'-methoxy-2'-naphthyl)-2-(1'-bromoethyl)-4,7-dihydro-1,3-dioxepine (1.09 g; 0.003 mol), cis-2-butene-1,4-diol (10 ml) and potassium acetate (0.40 g; 0.004 mol) is heated to 125° C. for 1 hour.

By following the procedure of Example 1a, there is obtained the title product (0.6 g; 0.0026 mol). Yield, 87%; m.p. 155°–156° C.

(1) A mixture of 2-(1'-bromoethyl)-2-(6'-methoxy-2'-naphthyl)-1,3-dioxolane (3.37 g; 0.01 mol), potassium acetate (1.2 g; 0.012 mol) and 2,2-dimethyl-1,3-propanediol (30 g) is heated to 150° C. for 24 hours.

By following the procedure of Example 1a, there is obtained the title product (1.61 g; 0.007 mol). Yield, 70% m.p. 155°–156° C.

EXAMPLE 2

2-(4'-methoxyphenyl)-propionic acid (a) A mixture of 2-bromo-1,1-dimethoxy-1-(4'-methoxyphenyl)-propane (2.89 g; 0.01 mol), calcium carbonate (1 g; 0.01 mol), methanol (7 ml) and water (3 ml) is refluxed for 35 hours. The reaction mixture is then cooled to 25° C. and worked up as described in Example 1a, there is so obtained the title product (1.69 g; 0.0094 mol). Yield, 94%; m.p. 55° C.

(b) A mixture of 2-bromo-1,1-dimethoxy-1-(4'-methoxyphenyl)-propane (2.89 g; 0.01 mol), potassium acetate (1.2 g; 0.012 mol), 1,2-propanediol (16 ml) and water (8 ml) is heated to 95° C. for 3 hours.

By following the procedure of Example 1a, there is obtained the title product (1.71 g; 0.0095 mol). Yield, 95%; m.p. 57° C.

(c) A mixture of 2-bromo-1,1-dimethoxy-1-(4'-methoxyphenyl)-propane (2.89 g; 0.01 mol), potassium acetate (1.2 g; 0.012 mol) and n-butanol (40 ml) is heated to 115° C. for 32 hours. By following the procedure of Example 1a, there is obtained the title product (1.60 g; 0.0089 mol). Yield, 89%; m.p. 56°–57° C.

(d) A mixture of 2-(1-bromoethyl)-2-(4'-methoxyphenyl)-1,3-dioxane (3.01 g; 0.01 mol), potassium acetate (1.2 g; 0.012 mol) and ethylene glycol (40 ml) is heated to 115° C. for 4 hours.

By following the procedure of Example 1a, there is obtained the title product (1.70 g; 0.0094 mol). Yield, 94%; m.p. 56°–57° C.

(e) A mixture of 2-(1-bromoethyl)-2-(4'-methoxyphenyl)-1,3-dioxane (3.01 g; 0.01 mol), potassium acetate (1.2 g; 0.012 mol) and 1,3-propanediol (40 ml) is heated to 115° C. for 4 hours.

By following the procedure of Example 1a, there is obtained the title product (1.73 g; 0.0096 mol). Yield, 96%; m.p. 57° C.

(f) A mixture of 2-(1'-bromoethyl)-2-(4'-methoxyphenyl)-1,3-dioxolane (2.87 g; 0.01 mol), potassium acetate (1.2 g; 0.012 mol) and ethylene glycol (40 ml) is heated to 115° C. for 15 hours.

By following the procedure of Example 1a, there is obtained the title product (1.44 g; 0.008 mol). Yield, 80%; m.p. 57° C.

(g) A mixture of 2-(1-bromoethyl)-5-(2'-butyl)-5-methyl-2-(4'-methoxyphenyl)-1,3-dioxane (3.68 g; 0.01 mol), ethylene glycol (40 ml) and potassium acetate (1.2 g; 0.012 mol) is heated to 125° C. for 4 hours.

By following the procedure of Example 1a, there is obtained the title product (1.7 g; 0.0094 mol). Yield, 94%; m.p. 56° C.

(h) A mixture of 2-(1'-bromoethyl)-2-(4'-methoxy)-4,7-dihydro-1,3-dioxepine (3.13 g; 0.01 mol), potassium acetate (1.2 g; 0.012 mol) and ethylene glycol (40 ml) is heated to 115° C. for 1 hour.

By following the procedure of Example 1a, there is obtained the title product (1.52 g; 0.0085 mol). Yield, 85%; m.p. 57° C.

(i) By substituting cis-2-butene-1,4-diol (40 ml) for ethylene glycol in Example 2h, and otherwise heating the reaction mixture to 125° C. for 3 hours and then following the procedure of Example 1a, there is obtained the title product (1.52 g; 0.0085 mol). Yield, 85%; m.p. 55°–57° C.

EXAMPLE 3

2-(4'-isobutylphenyl)-propionic acid (a) A mixture of 2-bromo-1,1-dimethoxy-1-(4'-isobutylphenyl)-propane (3.15 g; 0.01 mol), potassium acetate (12 g; 0.012 mol), n-butanol (12 ml), 1,2-propanediol (16 ml) and water is heated to 95° C. for 67 hours.

By following the procedure of Example 1a, there is obtained the title product (1.75 g; 0.0085 mol). Yield, 85%; m.p. 76°–77° C.

(b) By substituting ethylene glycol (100 ml) for n-butanol, 1,2-propanediol and water in the procedure of Example 3a, and otherwise heating the reaction mixture to 125° C. for 16 hours and then following the procedure of Example 1a, there is obtained the title product (1.64 g; 0.008 mol). Yield, 80%; m.p. 76°–77° C.

(c) A mixture of 2-(1'-bromoethyl)-5,5-dimethyl-2-(4'-isobutylphenyl)-1,3-dioxane (3.55 g; 0.01 mol), potassium acetate (1.29 g; 0.012 mol) and cis-2-butene-1,4-diol (40 ml) is heated to 125° C. for 3 hours.

By following the procedure of Example 1a, there is obtained the title product (1.93 g; 0.0093 mol). Yield, 93%; m.p. 77° C.

(d) A mixture of 2-(1'-bromoethyl)-2-(4'-isobutylphenyl)-4,7-dihydro-1,3-dioxepine (3.39 g; 0.01 mol), potassium acetate (1.2 g; 0.012 mol) and ethylene glycol (50 ml) is heated to 115° C. for 25 hours.

By following the procedure of Example 1a, there is obtained the title compound (1.89 g; 0.0092 mol). Yield, 92%; m.p. 77° C.

(e) By substituting cis-2-butene-1,4-diol, (40 ml) for ethylene glycol in the procedure of Example 3d, and otherwise heating the reaction mixture to 125° C. for 3 hours and then following the procedure of Example 1a, there is obtained the title product (1.85 g; 0.009 mol). Yield, 90%, m.p. 76°–77° C.

(f) A mixture of 2-(1'-bromoethyl)-5,5-dimethyl-2-(4'-isobutyl)-1,3-dioxane (3 55 g; 0.01 mol), potassium acetate (1.2 g; 0.012 mol) and 2,2-dimethyl-1,3-propanediol (30 g) is heated to 150° C. for 24 hours.

By following the procedure of Example 1a, there is obtained the title product (1.4 g; 0.007 mol). Yield, 70%; m.p. 76°-77° C.

(g) A mixture of 2-(1'-chloroethyl)-5,5-dimethyl-2-(4'-isobutylphenyl)-1,3-dioxane (68.4 g; 0.23 mol), ethylene glycol (92,5 ml), 2,2-dimethyl-1,3-propanediol (36 g) and potassium acetate is heated to 195° C. for 2 hours.

The mixture is then cooled to 90° C. and worked up as described in Example 1a to afford the title product (23.1 g; 0.112 mol).

Yield, 48% m.p. 76°-77° C.

EXAMPLE 4

4'-methoxyphenyl-acetic acid

A mixture of 2-bromoethyl-2-(4'-methoxyphenyl)-4,7-dihydro-1,3-dioxepine (2.99 g; 0.01 mol), potassium acetate (1.2 g; 0.012 mol) and cis-2-butene-1,4-diol (40 ml) is heated to 125° C. for 3 hours.

By following the procedure of Example 1a, there is obtained the title product (1.5 g; 0.009 mol). Yield, 90%; m.p. 86°-87° C.

EXAMPLE 5

2-(5'-bromo-6'-methoxy-2'-naphthyl)-propionic acid

A mixture of 2-(1-bromoethyl)-5,5-dimethyl-2-(5'-bromo-6'-methoxy-2'-naphthyl)-1,3-dioxane (4.58 g; 0.01 mol), potassium acetate (1.2 g; 0.012 mol) and ethylene glycol (40 ml) is heated to 125° C. for 24 hours.

By following the procedure of Example 1a, there is obtained the title product (2.8 g; 0.009 mol). Yield, 90%; m.p. 161°-163° C.

EXAMPLE 6

2-(2'-thienyl)-propionic acid

A mixture of 2-(1'-bromoethyl)-5,5-dimethyl-2-(2'-thienyl)-1,3-dioxane (28.7 g; 0.094 mol), ethylene glycol (32.5 g; 0.52 mol), 2,2-dimethyl-1,3-propanediol (13.75 g; 0.13 mol) and potassium acetate (10.25 g; 0.11 mol) is heated to 150° C. for 5 hours.

By following the procedure of Example 1a, there is obtained the title product (11.7 g; 0.075 mol). Yield, 80%; b.p. 98°-100° C./0.5 mm Hg.

We claim:

1. A process for preparing an alpha-arylalkanoic acid or a salt thereof, which comprises the rearrangement of an alpha-halo-alkylarylketal of formula

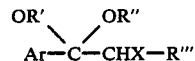

wherein

Ar is an aromatic ring selected from the group comprising (a) a phenyl ring substituted by one or two substituents slected from the group comprising halogen, 1-6 C alkyl, 1-4 C alkoxy, 2-4 C alkenyloxy, phenyl, phenoxy, dichlorophenoxy, dichloroanilino, benzoyl, indolinyl, dihydropyrrolyl, thenoyl (b) a naphthyl ring substituted by one or two substituents selected from the group comprising halogen and 1-4 C alkoxy (c) a pyrrolyl ring substituted by one or two radicals selected from the group comprising 1-4 C alkyl and alkyl$_{1-4}$ c-phenyl, (d) chlorocarbazolyl, (e) benzoxazolyl substituted by one chlorophenyl radical, and (f) thiazolyl substituted by one or two radical selected from the group comprising phenyl and chlorophenyl and (g) thienyl, R' and R", independently from each other, are a satured or unsatured, straight or branched alkyl radical having from 1 to 12 C atoms or, when taken together, are a satured or unsatured straight or branched alkylene radical having from 2 to 12 C atoms which completes an alicyclic ring having from 5 to 7 members;

X is halogen;

R''' is hydrogen, alkyl having from 1 to 6 C atoms or cycloalkyl having from 3 to 7 C atoms. in neutral or weakly alkaline conditions and in the presence of a polar-protic medium and the subsequent hydrolysis of the thus obtained ester in the same reaction medium to afford the corresponding alpha-arylalkanoic acid or a salt thereof.

2. A process according to claim 1, wherein the polar protic medium is consisting of water, an alcohol or a mixture thereof.

3. A process according to claim 2, wherein the alcohol is selected from the group comprising $C_1$–$C_{12}$ primary, secondary and tertiary alcohol and $C_2$–$C_{12}$ polyhydric alcohols.

4. A process according to claim 1, wherein the neutral or weakly alkaline condition is obtained by adding a buffer, an organic or inorganic weak base or a mixture thereof.

5. A process according to claim 1, wherein the ester is hydrolyzed by means of a base to afford a salt of the corresponding alpha-arylalkanoic acid which, when desired, is treated with an acid to afford the free alpha-arylalkanoic acid.

6. A process according to claim 1, wherein the ester is hydrolyzed by means of an acid to afford the corresponding alpha-arylalkanoic acid.

* * * * *